(12) United States Patent
Mousa

(10) Patent No.: US 6,866,864 B2
(45) Date of Patent: Mar. 15, 2005

(54) COMPOSITIONS AND METHODS OF USE IN THE TREATMENT OF ANGIOGENESIS AND VASCULAR-RELATED DISORDERS

(75) Inventor: Ahmed Mousa, 7 Linden Cir., Lincoln Univ., PA (US) 19352

(73) Assignee: Ahmed Mousa, Wynantskill, NY (US)

(*) Notice: Subject to any disclaimer, the term of this patent is extended or adjusted under 35 U.S.C. 154(b) by 410 days.

(21) Appl. No.: 09/824,174

(22) Filed: Apr. 2, 2001

(65) Prior Publication Data

US 2001/0053356 A1 Dec. 20, 2001

Related U.S. Application Data

(63) Continuation-in-part of application No. 09/531,297, filed on Mar. 20, 2000, now abandoned.

(51) Int. Cl.[7] .............................. A61K 9/48; A61F 2/00; A61F 13/00
(52) U.S. Cl. ........................ 424/457; 424/422; 424/434; 424/435; 424/464; 424/725; 424/754; 424/423; 424/449; 514/458; 514/825
(58) Field of Search ................................ 424/400, 725, 424/754, 422, 435, 434, 423, 622, 436, 451, 464, 449; 516/458, 825

(56) References Cited

U.S. PATENT DOCUMENTS

| | | | | |
|---|---|---|---|---|
| 5,332,579 A | * | 7/1994 | Umbdenstock | 424/639 |
| 5,883,086 A | * | 3/1999 | Craft | 514/168 |
| 5,972,985 A | * | 10/1999 | Thomas et al. | 514/400 |
| 6,048,846 A | * | 4/2000 | Cochran | 514/168 |
| 6,133,317 A | * | 10/2000 | Hart | 514/574 |

* cited by examiner

*Primary Examiner*—James M. Spear
*Assistant Examiner*—Liliana Di Mola--Baron

(57) ABSTRACT

The present invention provides compositions and method of use for the prevention and treatment of vascular-related disorders such as vascular re-occlusion or restenosis post-coronary intervention with balloon angioplasty or stent procedures and diseases associated with pathological angiogenesis such as cancer, ocular or inflammatory diseases. More specifically, compositions and methods of the present invention involve the combination of the garlic-derived or related compounds and antioxidants.

11 Claims, 15 Drawing Sheets

(8 of 15 Drawing Sheet(s) Filed in Color)

*Effect of the Garlic Ingredient, Alliin With and Without the Antioxidant Vitamins C & E on $FGF_2$-Induced Human Endothelial Cell Tube Formation*

Data represent mean % inhibition ± SEM, n = 3
Vitamins C & E were added at fixed 2.5 µg each

*Anti-Angiogenic Efficacy of the Garlic Ingredient, Alliin in Inhibiting $FGF_2$-Induced Angiogenesis in the Chick CAM Model*

Representative images illustrating the increase in new blood vessels from pre-existing ones by $FGF_2$ and its potent inhibition by Alliin. Data represent mean ± SEM, n=6, **p<0.001

*Inhibitory Efficacy of the Garlic Ingredient, Alliin With and Without the Antioxidant Vitamins C & E on $FGF_2$-Induced Angiogenesis in the CAM Model*

Data represent mean ± SEM, n = 8 per group
Vitamins C & E were used at fixed 2.5-μg each

*Effect of the Garlic Ingredient, Alliin on the Secretion of $FGF_2$ from Human Fibrosarcoma Tumor Cells*

The garlic ingredient, Alliin inhibited in a dose dependent manner $FGF_2$ secretion from human fibrosarcoma tumor cells.

**p < 0.001

*Effect of the Garlic Ingredient, Alliin on the Secretion of VEGF from Human Fibrosarcoma Tumor Cells*

The garlic ingredient, Alliin inhibited in a dose dependent manner VEGF secretion from human fibrosarcoma tumor cells.

\*p < 0.01
\*\*p < 0.001

COMPOSITIONS AND METHODS OF USE IN THE TREATMENT OF ANGIOGENESIS AND VASCULAR-RELATED DISORDERS

The present invention is a continuation-in-part of U.S. Ser. No. 09/531,297, filed Mar. 20, 2000, now abandoned.

FIELD OF THE INVENTION

The present invention relates to the treatment and prevention of vascular-related disorders such as vascular re-occlusion or restenosis post-arterial intervention procedures (balloon angioplasty or stent) and pathological angiogenesis-mediated disorders such as cancer, diabetic retinopathy, macular degeneration, and inflammatory diseases. More particularly, the present invention is directed to compositions and methods of use in the treatment and prevention of such diseases. The methods of the present invention involve the administration to mammals a combination of (i) garlic derived sulfhydryl or sulfate containing or related compounds, (ii) antioxidants, and optionally (iii) minerals. Preferred methods of the present invention involve the oral administration of compositions comprising one or more garlic related compounds, one or more antioxidants and one or more minerals. Other preferred embodiments of the present invention involve the prevention and treatment of vascular-related disorders (vascular restenosis), cancer, diabetic retinopathy (DR), age-related macular degeneration (AMD) and inflammatory diseases through the combined administration of the garlic compound alliin, or other natural sulfhydryl-containing compounds, natural antioxidants such as vitamin E, C, and minerals such as selenium. This combined composition could be used as a supplement for patients with vascular arterial disorders for pre- and post-arterial (coronary, carotid or peripheral arteries) interventional procedures and for cancer patients taking cancer chemotherapeutics, radiotherapy, and other angiogenesis inhibitors. Additionally, this supplement could be used in conjunction with laser therapy and other angiogenesis inhibitor therapy for patients with DR or AMD. The combined composition could also be used in conjunction with chemotherapy, radiation, laser, other angiogenesis inhibitors, or anti-restenosis agents.

BACKGROUND OF THE INVENTION

Garlic has been used in herbal medicine for thousands of years. Most studies on garlic during the past 15 years have been primarily in the field of cardiovascular. Cardiovascular studies have been mainly related to atherosclerosis, where effects of different garlic preparations garlic were examined on serum cholesterol, LDL, HDL, triglyceride, and oxidative stress. Agarwal, *Med. Res. Rev.* 16 (1): 111–124 (1996), Berthold and Sudhop, *Curr. Opin. Lipido.* 9 (6): 565–569 (1998); Ide and Lau, *Phytomedicine* 6 (2): 125–131 (1999). Although the studies were not consistent in relation to the dosage, standardization of garlic preparations, and period of treatment, most findings suggest but not strongly indicate that garlic decreases cholesterol and triglyceride levels in patients with increased levels of these lipids. Lowering of serum lipids by garlic ingestion may decrease the atherosclerosis process. The role of smooth muscle cell migration, proliferation in accelerated atherosclerosis and restenosis in ischemic heart disease patients was previously documented (*J. American College Cardiology* 15 (7): 1667–1687, 1990 and *Human Pathology* 18 (3): 240–247, 1987). Additionally, several studies showed antiplatelet effects for different garlic preparations and active ingredients, suggesting potential anti-thrombotic benefits (Apitz-Castro et. al., *Thromb. Res.* 75 (3): 243–249 (1994). The present investigation examined the possible role of garlic ingredients on smooth muscle cell migration toward plasma obtained from acute myocardial infarction I) patients during balloon angioplasty and stent coronary intervention & on the modulation of angiogenesis-mediated disorders.

Angiogenesis is the development of new blood vessels from preexisting blood vessels. Physiologically, angiogenesis ensures proper development of mature organisms, prepares the womb for egg implantation and plays a key role in wound healing. On the other hand, angiogenesis supports the pathological conditions associated with a number of disease states such as cancer, inflammation and ocular diseases (DR and AMD).

The development of vascular networks during embryogenesis or normal and pathological angiogenesis depends on growth factors and cellular interactions with the extracellular matrix (see Breier and Risau, Trends in Cell Biology, 6: 454–456(1996); Folkman, *Nature Medicine* 1:27–31(1995); Risau, *Nature* 386:671–674 (1997)). Blood vessels arise during embryogenesis by two processes: vasculogenesis and angiogenesis. Blood et al., *Bioch. Biophys. Acta,* 1032: 89–118 (1990). VEGF, bFGF, IL-8 and TNF-a are some of the growth factors that play a role in pathological angiogenesis associated with solid tumors, diabetic retinopathy, and rheumatoid arthritis. Folkman et al., *Science,* 235: 442–447 (1987). Angiogenesis is generally absent in adult or mature tissues, although it does occur in wound healing and in embryogenesis. Moses et al., *Science,* 248: 1408–1410 (1990).

Angiogenesis or "neovascularization" is a multi-step process controlled by the balance of pro- and anti-angiogenic factors. The latter stages of this process involve proliferation and the organization of endothelial cells (EC) into tube-like structures. Growth factors such as FGF2 and VEGF are thought to be key players in promoting EC growth and differentiation. The ECs is the pivotal component of the angiogenic process and responds to many cytokines through its cell surface receptors and intracellular signaling mechanisms. ECs in culture are capable of forming tube-like structures that possess lumens. Therefore, ECs are not only a prerequisite for neovascularization, but appear to be the basal structural requirement as well.

Angiogenesis-dependent diseases include the following: Inflammatory disorders such as immune and non-immune inflammation, rheumatoid arthritis, psoriasis; ocular disorders such as diabetic retinopathy, neovascular glaucoma, retinopathy of prematurity, age-related macular degeneration, corneal graft rejection; cancer associated disorders such as solid tumors, tumor metastases, and blood born tumors such as leukemia, angiofibroma, kaposi sarcoma, benign tumors, as well as other cancers, which require neovascularization to support tumor growth.

It has been proposed that inhibition of angiogenesis would be a useful therapy for restricting tumor growth. Inhibition of angiogenesis can be achieved by inhibiting endothelial cell response to angiogenic stimuli as suggested by Folkman et al., *Cancer Biology,* 3:89–96 (1992), where it was described examples of those endothelial cell response inhibitors such as angiostatic steroids, fungal derived products such as fumagilin, platelet factor 4, thrombospondin, alpha-interferon, vitamin D analogs, and D-penicillamine. For additional proposed inhibitors of angiogenesis, see Blood et. al., *Bioch. Biophys. Acta.,* 1032:89–118 (1990), Moses et al., *Science,* 248: 1408–1410 (1990), and U.S. Pat. Nos. 5,092, 885, 5,112,946, 5,192,744, and 5,202,352. None of the inhibitors of angiogenesis described in the foregoing references target the use of garlic active ingredients in combination with antioxidants, and minerals for the inhibition of angiogenesis.

The inclusion of garlic in "nutraceutical" compositions has been previously proposed. For example, U.S. Pat. Nos. 5,883,086 (Craft) and 6,048,846 (Cochran) disclose compositions comprising the steroid hormone, dehydroepiandrosterone (DHEA), and optionally garlic. The '086 and '846 compositions are prescribed for the alleviation of an irregular heartbeat, the symptoms of stress and for lowering blood pressure in humans; and which modulate the physiological conditions within the body, respectively. U.S. Pat. No. 6,133,317 (Hart) discloses oxalic acid or oxalate compositions optionally further comprising garlic, for use in treating a myriad of ailments. U.S. Pat. No. 5,972,985 (Thomas et al.) discloses antioxidant compositions comprising a form of histidine and a group of antioxidant phytonutrients, e.g., garlic, for the treatment of a myriad of diseases. U.S. Pat. No. 5,332,579 discloses compositions comprising enzyme activating substances (i.e., magnesium), enzyme co-factors (i.e., B vitamins), an herbal antispasmodic substance (e.g., Valerian root), zinc and Vitamin C, for the treatment of alcoholic related disorders. The present invention compositions do not contain hormones, steroids, oxalic acid or oxalate, forms of histidine or antispasmodic substances.

BRIEF DESCRIPTION OF DRAWINGS

The patent or application file contaínes at least one drawing executed in color. Copies of this patent or patent application publication with color drawings will be provided by the office upon request and payment of the necessary fee.

The procedure is as follow: 20 $\mu$l plasma was placed in the bottom chamber (A), smooth muscle suspension $1\times10^6$ cells in 5 $\mu$l with or without the various garlic active ingredients, antioxidants or combinations were placed in the top chamber (B). The chamber B was fitted over chamber A, covered and placed in a CO2 (5%)/O2 (95%) incubator for 22 hours at 37° C. The filter from chamber B was taken out of the chamber and the cells on the top were scraped off using a cell scraper. The filter was placed in formaldehyde, Triton X100, washing buffer solution, stained with Rhodamine phloyden, and then a washing solution as shown in station C (front view) and D (side view). The filter was then dried and put in a fluorescence plate reader to read the degree of fluorescence.

Figure 2:
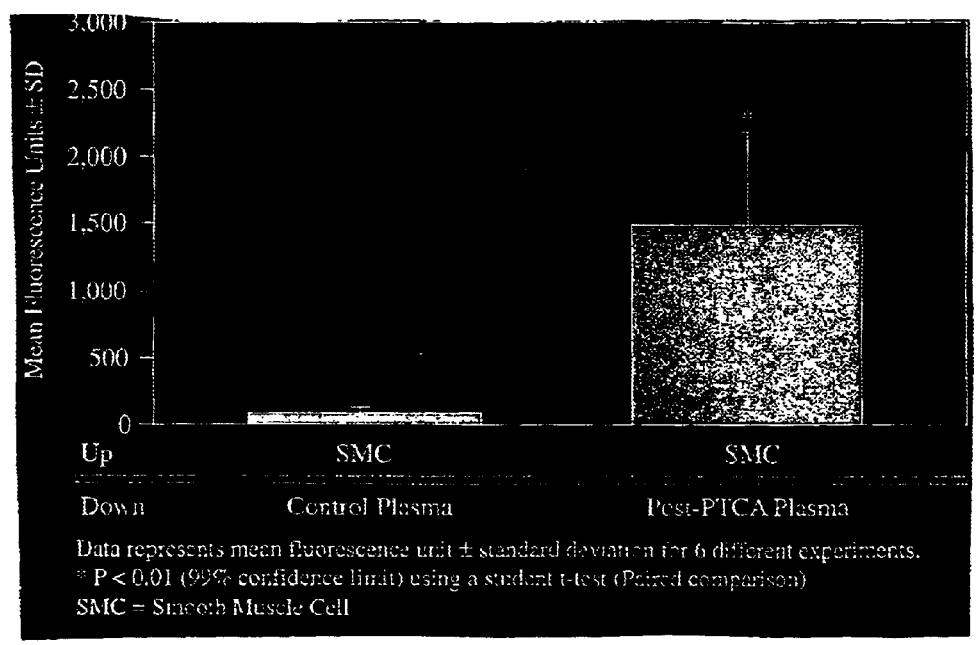

FIG. 2. Graph showing the significant and distinct increase in smooth muscle cell migration toward plasma obtained from MI as compared to normal healthy subjects.

Figure 3:
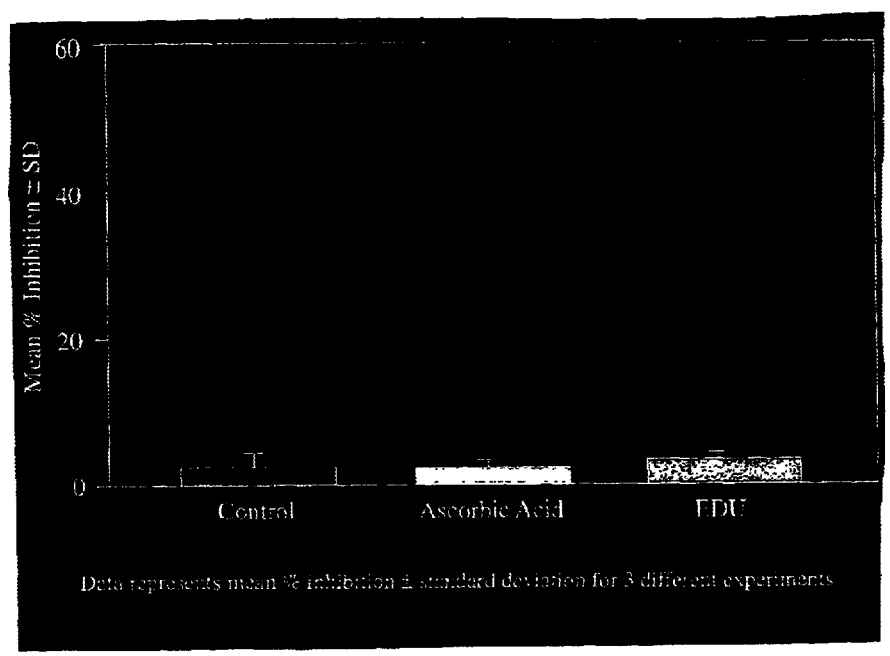

FIG. 3. Graph showing the lack of effect of the antioxidants, ascorbic acid (vitamin C) and synthetic ethylene diphenyl urea (EDU) at 3 $\mu$M each, on human smooth muscle cell migration toward plasma obtained from MI patients during balloon angioplasty and stent coronary intervention.

Figure 4:
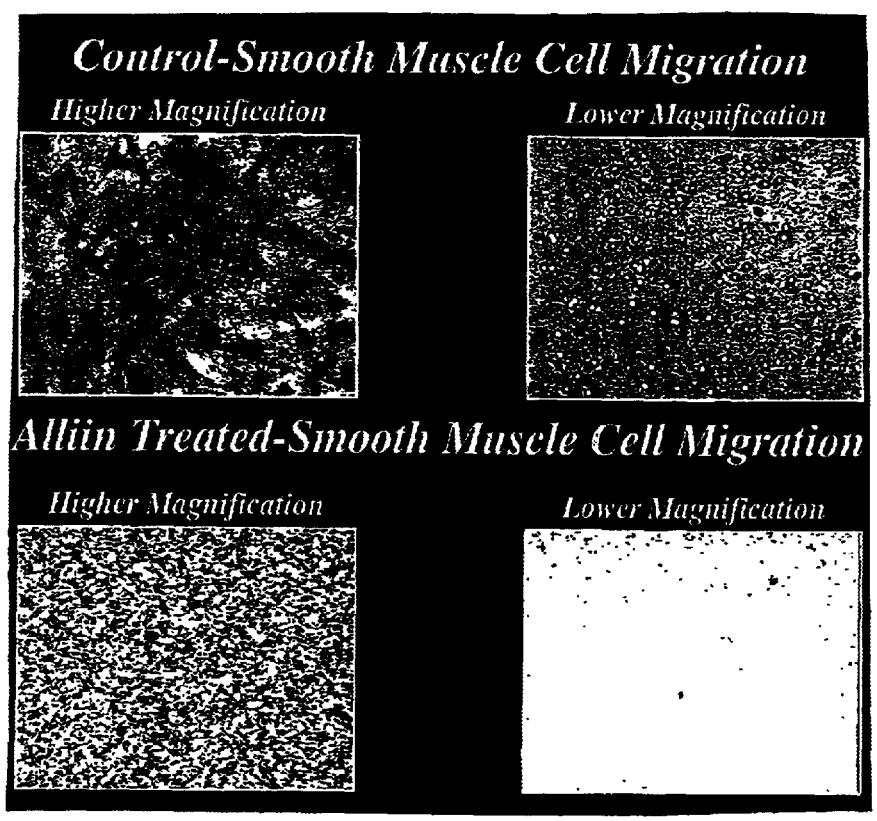

FIG. 4. Graph showing an illustration (higher and lower magnification) of migrated human smooth muscle toward plasma from plasma obtained from MI subjects treated with the garlic ingredient Alliin or untreated. Inhibition of smooth muscle cell migration by Alliin is qualitatively demonstrated.

Figure 5:
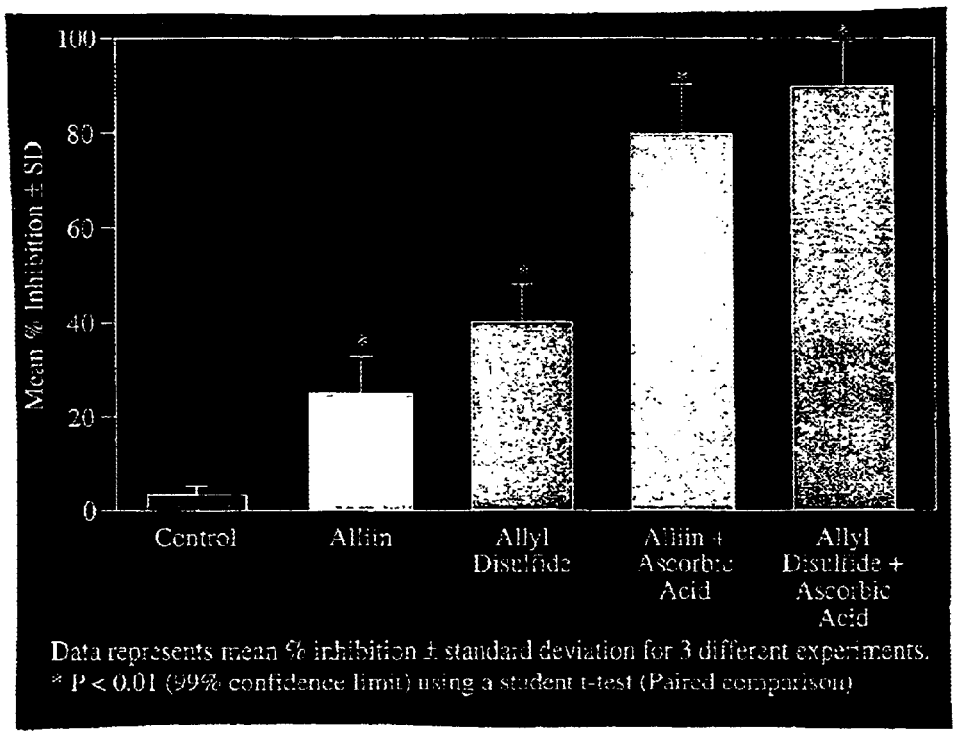

FIG. 5. Graph showing the synergy between garlic ingredients (alliin, allyl disulfide) at 1 $\mu$M each and the antioxidant, ascorbic acid (3 $\mu$M), on the inhibition of human smooth muscle cell migration toward plasma from MI patients during balloon angioplasty and stent coronary intervention. Similar synergy was shown with other antioxidants.

Figure 6:
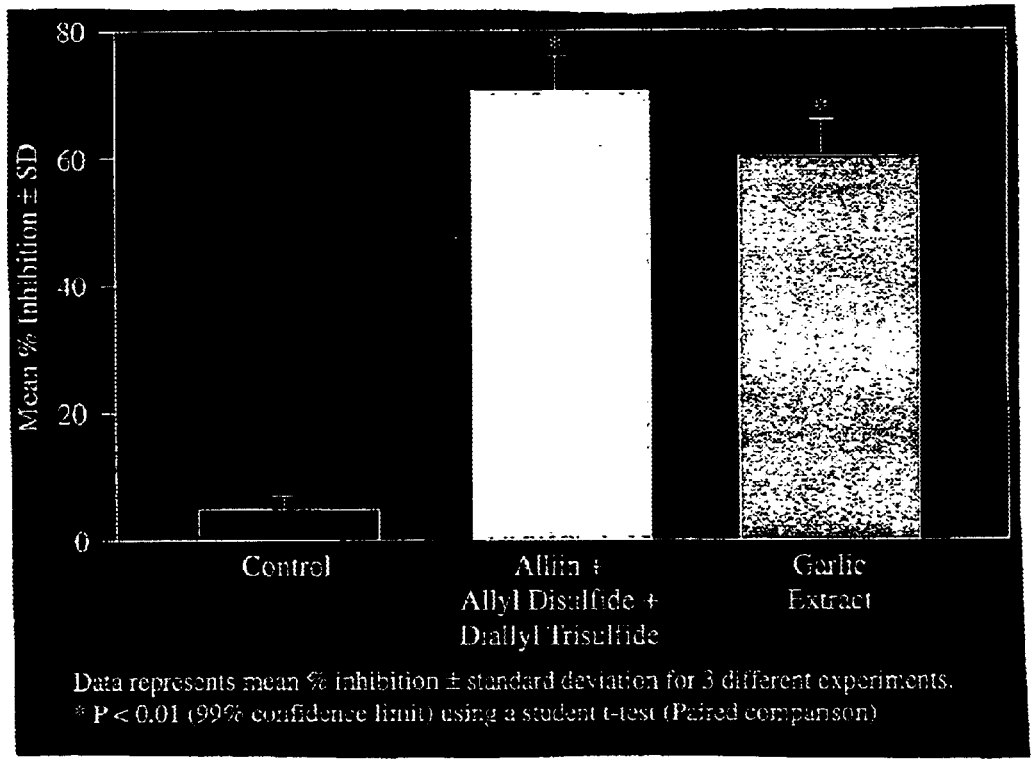

FIG. 6. Graph showing the inhibitory efficacy of sulfur containing garlic ingredients as well garlic extract on smooth muscle cell migration toward plasma from MI patients during balloon angioplasty and stent coronary intervention.

Figure 7:
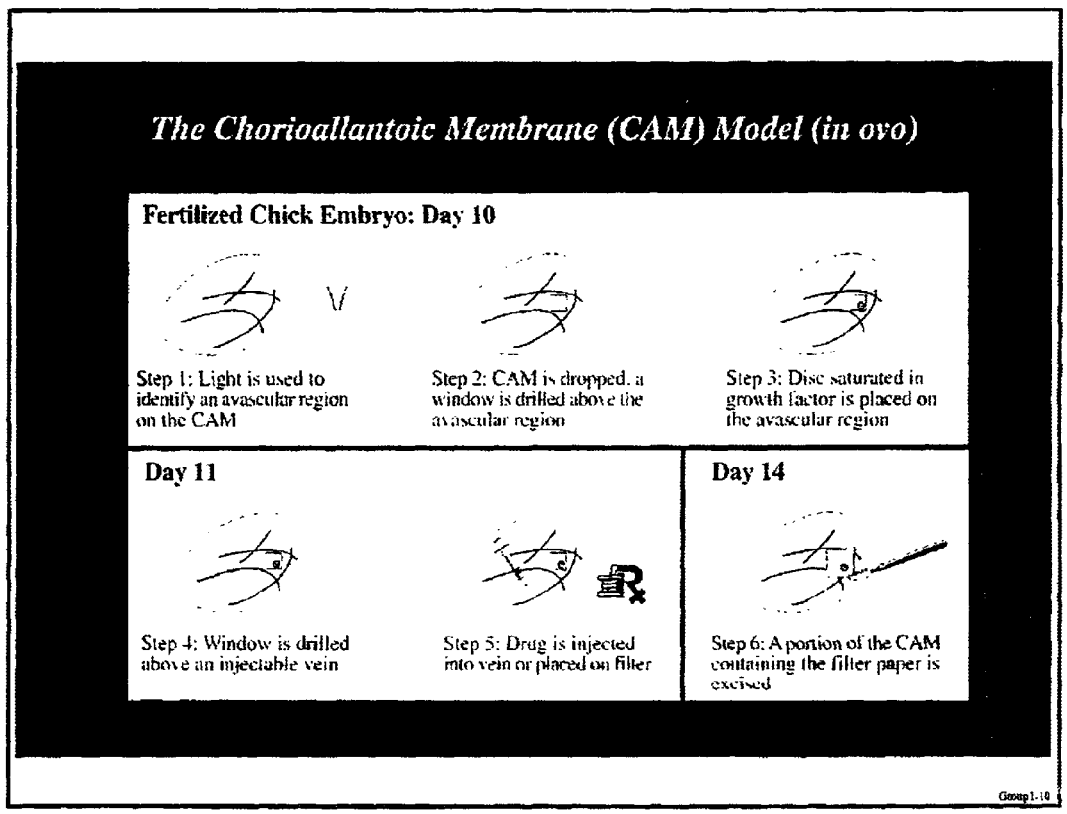

FIG. 7. Diagrammatic sketch showing the steps involved in the in vivo chorioallantoic membrane (CAM) model.

Figure 8:
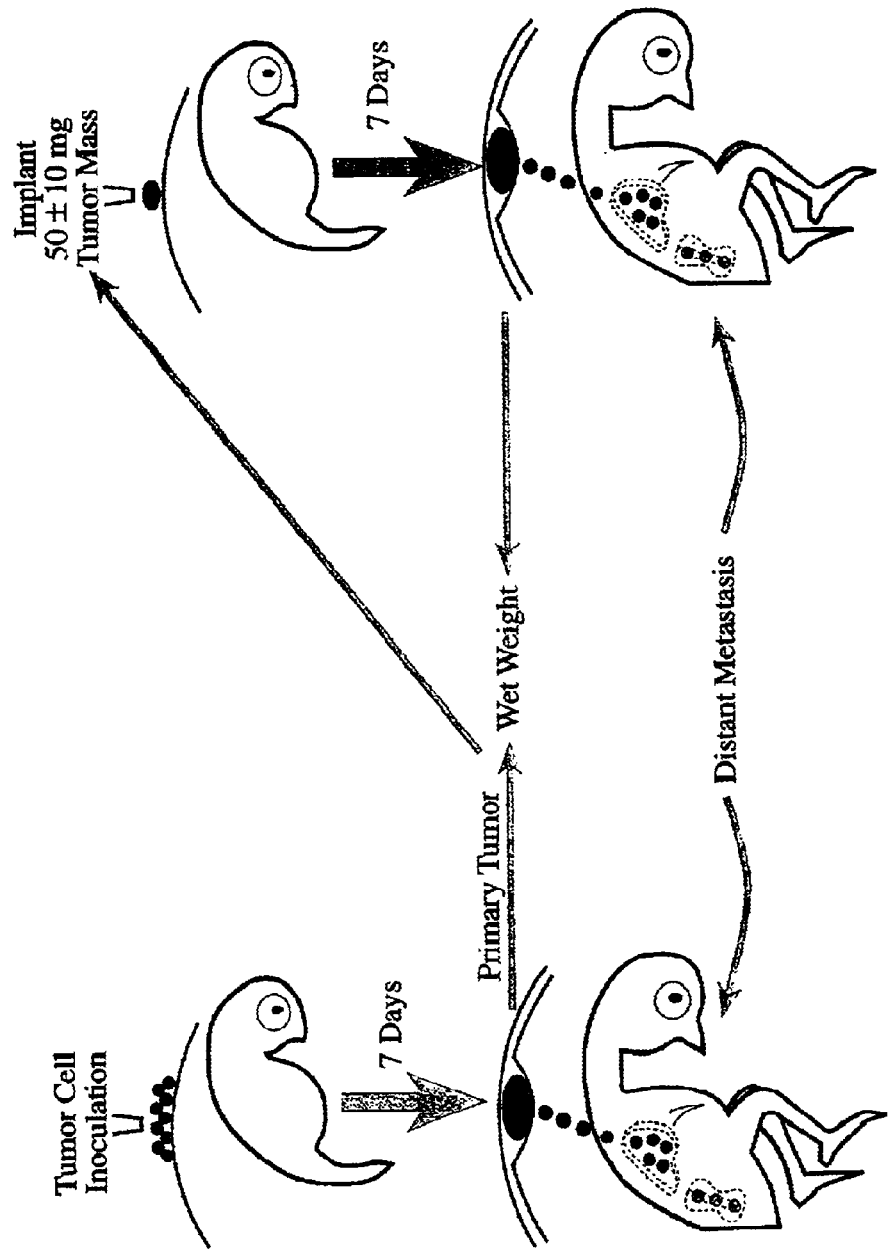
Figure 9:
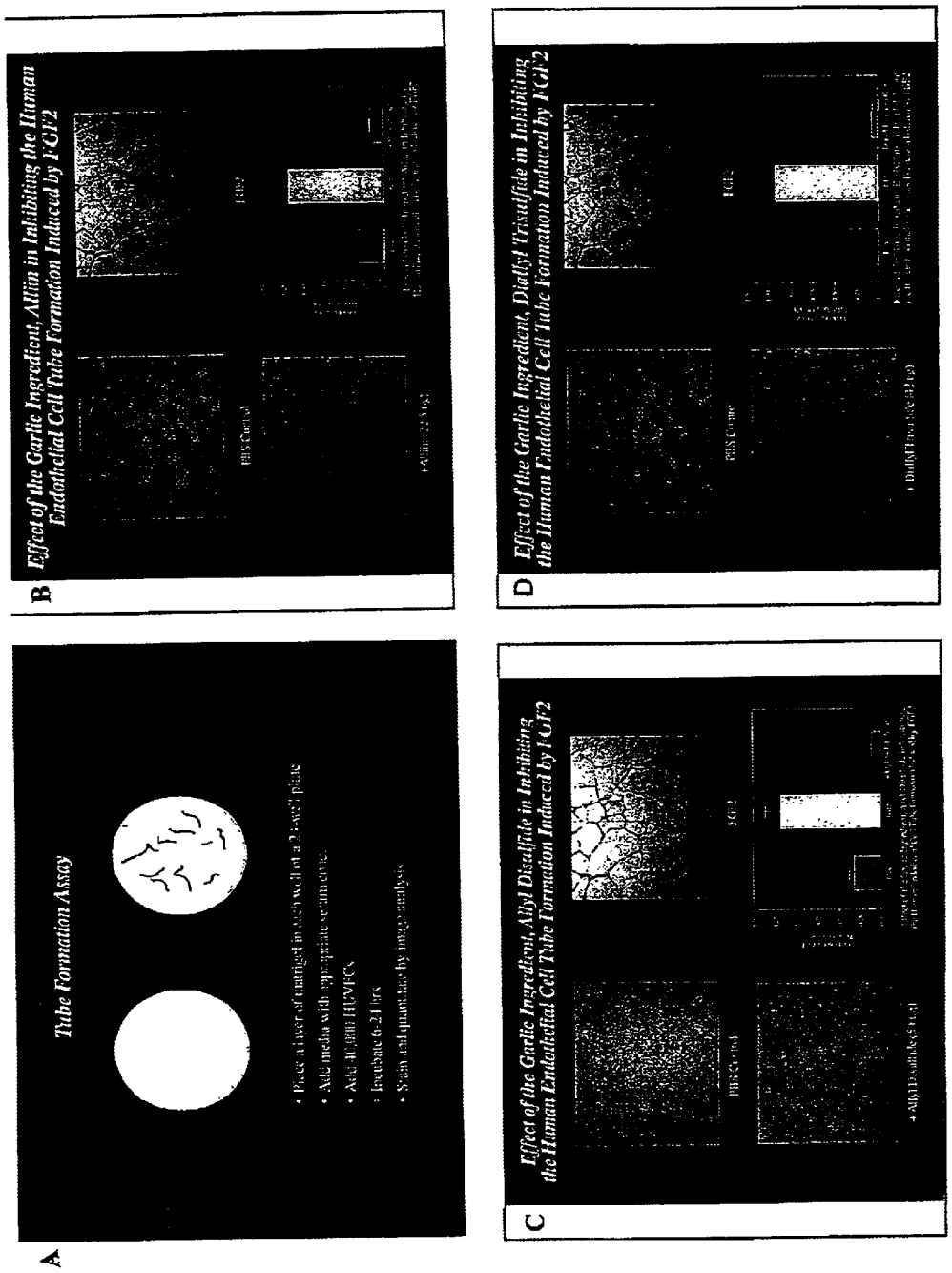

FIG. 8. Diagrammatic sketch showing the steps involved in the in vivo tumor growth model in the chorioallantoic membrane (CAM) model FIG. 9. Protocol for human endothelial tube formation assay is as shown in the sketch (A). Effect of the different garlic ingredients including Alliin at 22.5 $\mu$g (B), Allyl disulfide at 50 $\mu$g (C), and Diallyl trisulfide at 42 $\mu$g (D) on human endothelial cell tube formation induced by FGF2 (12.5 ng). Figure shows representative illustration of the PBS control, FGF2 stimulated and FGF2+garlic ingredients. Data represent mean±SEM, n=3.

Figure 10:
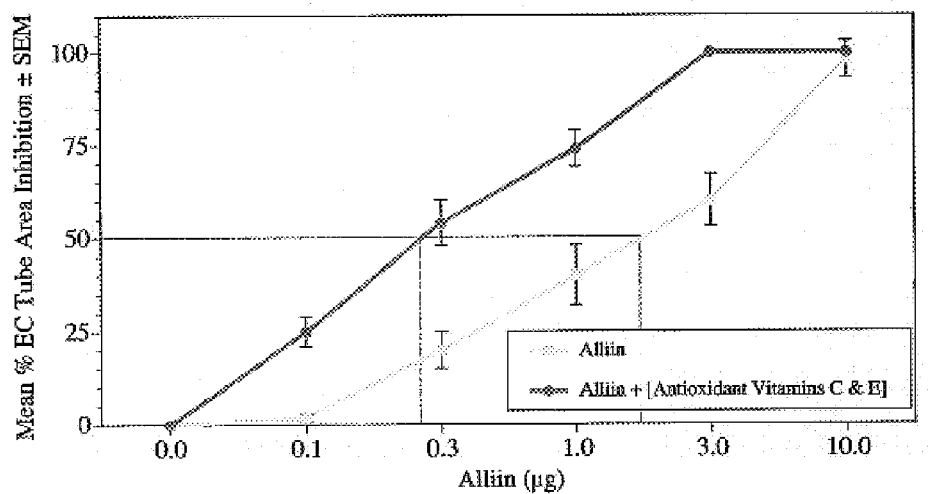

FIG. 10. Concentration-dependent efficacy of Alliin±antioxidants on FGF2-induced EC tube formation. Data represent mean±SEM, n=6.

Figure 11:
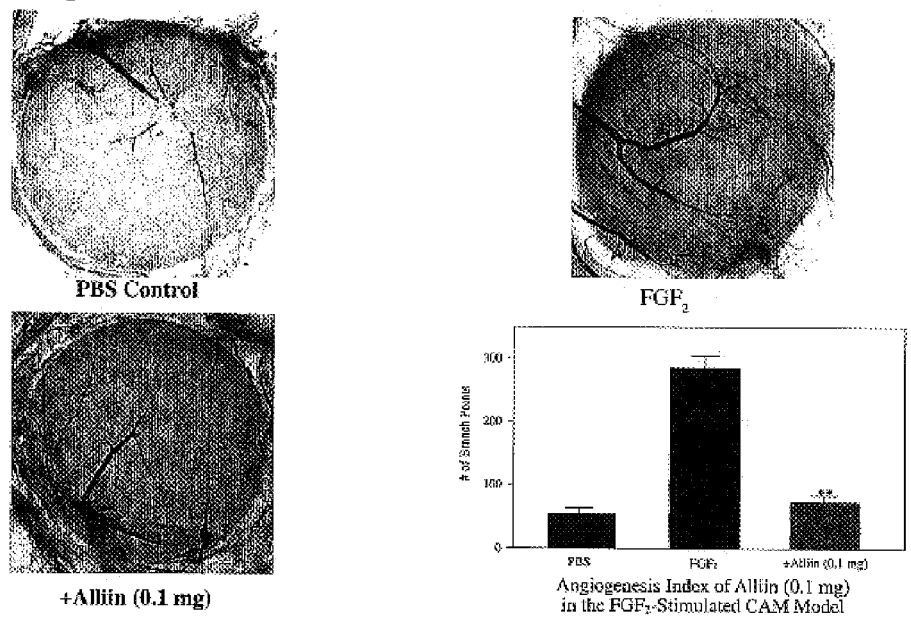
Figure 11:
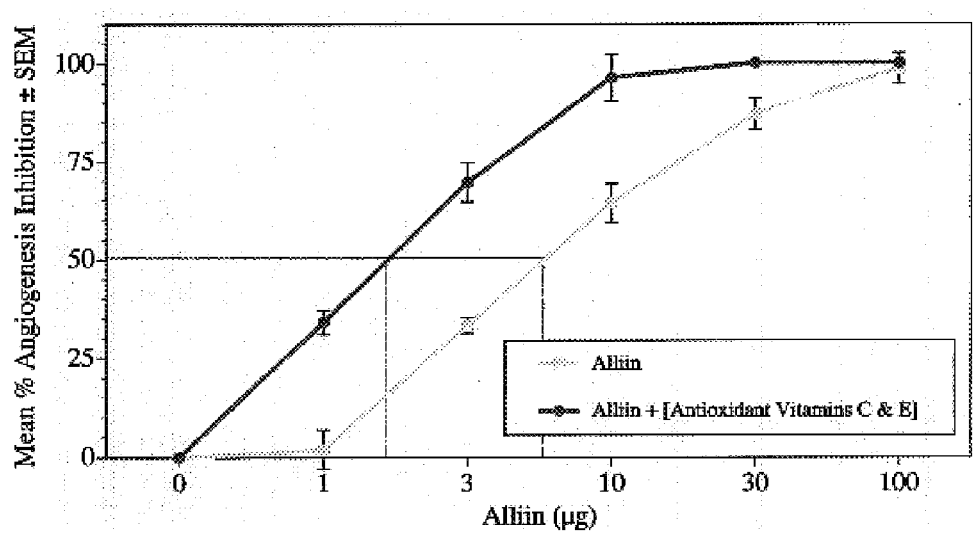

FIG. 11A. Effect of the garlic ingredient, Alliin (0.11 mg) on angiogenesis-induced by FGF2 (1.0 $\mu$g) in the CAM model. Representative illustration of control, FGF2 stimulated and FGF2+Alliin (0.11 mg) treated. Data represent mean±SEM, n=6, ** P<0.001. FIG. 11B. Dose-dependent efficacy of Alliin±antioxidants on FGF2-induced angiogenesis in the CAM model. Data represent mean % inhibition±SEM, n=6

Figure 12:
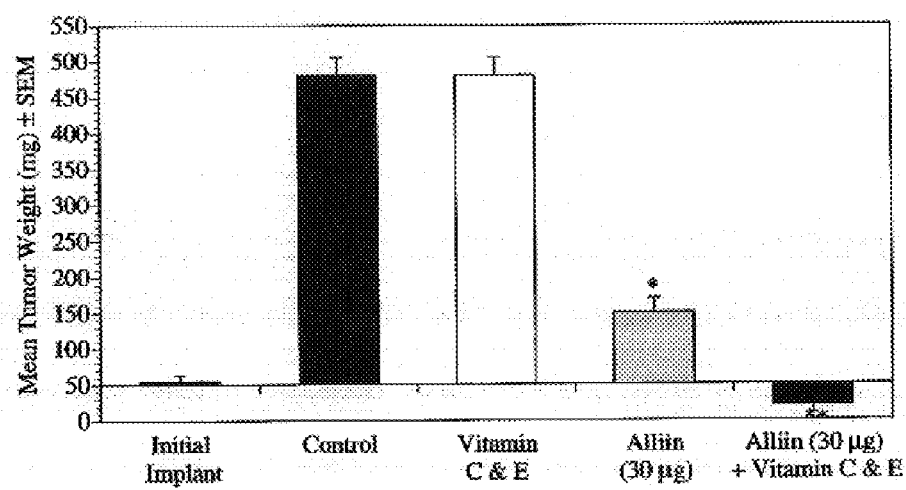
Figure 12:
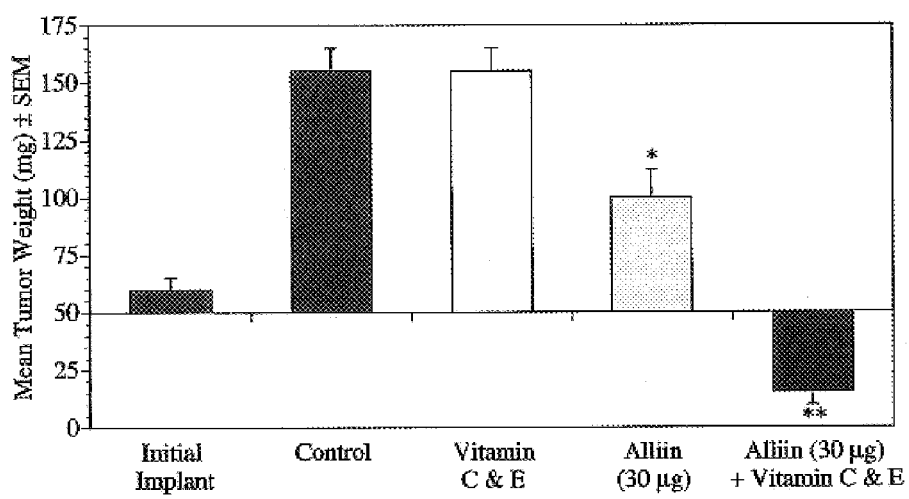

FIG. 12A. Effect of the garlic ingredient, Alliin±antioxidants on human Fibrosarcoma tumor growth in the CAM tumor implant model. FIG. 12B. Effect of the garlic ingredient, Alliin±antioxidants on human colon tumor growth in the CAM model. Data represent mean tumor weight (mg)±SEM, ** P<0.001.

Figure 13:
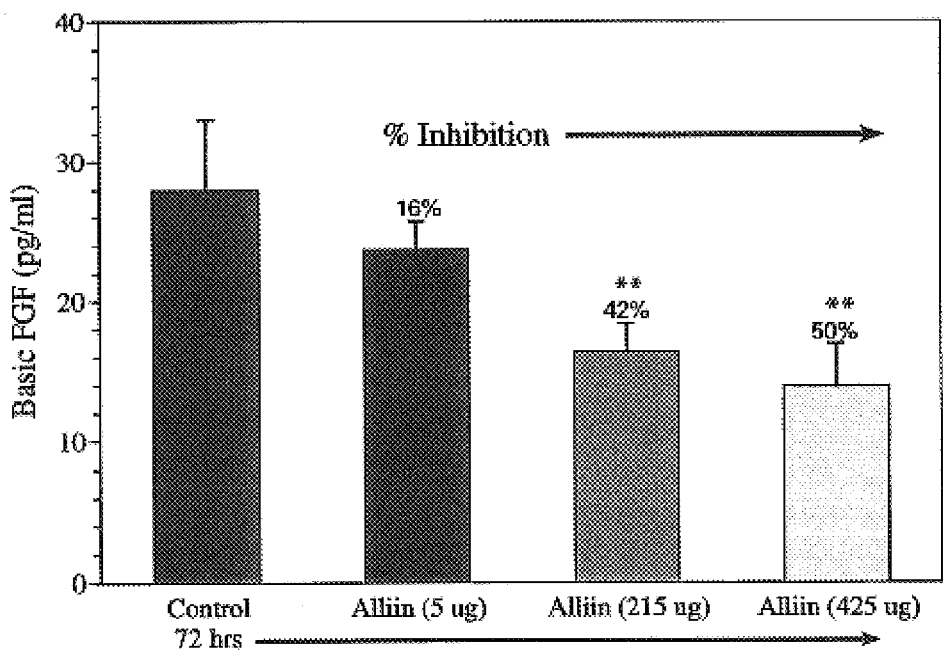
Figure 13:
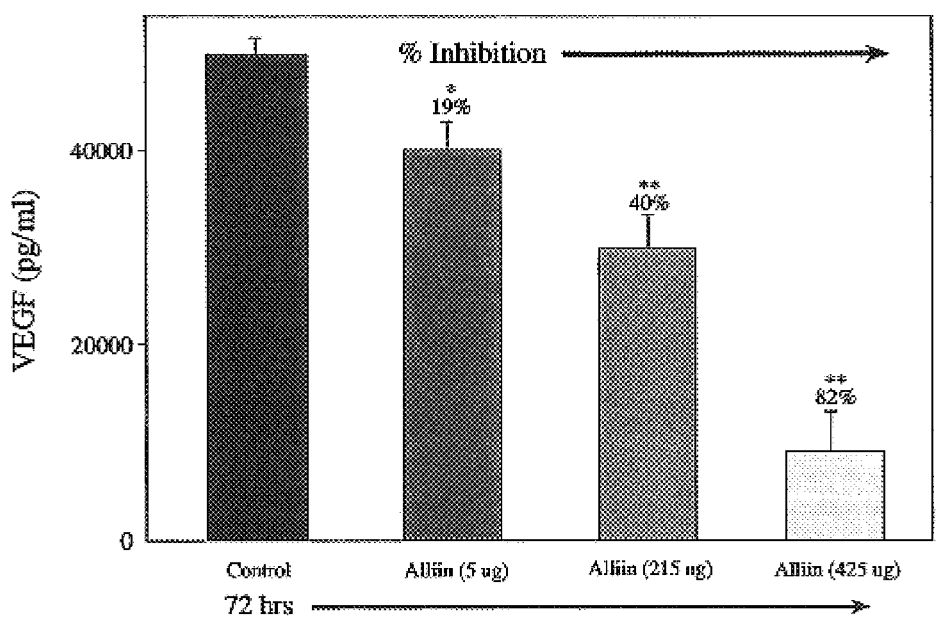

FIG. 13. Effect of the garlic ingredient Alliin (5–425 $\mu$g) on the secretion of either FGF-2 (A) or VEGF (B) from human fibrosarcoma cells after 72 hours of incubation at 37° C. Data represent mean release of FGF2 or VEGF (pg/ml) ±SEM, n=3, ** P<0.001.

Figure 14:
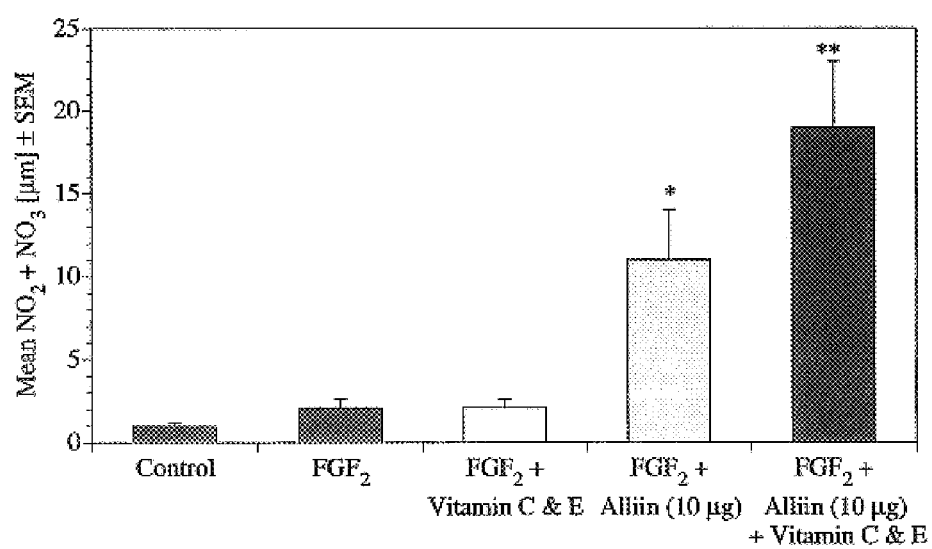

FIG. 14. Graph showing the effect of Alliin+antioxidant on nitric oxide levels in the CAM fluid at 48 hours after treatment. The assay used measured nitrate and nitrite levels. Data represent mean nitrate and nitrite±SEM, n=3,  P<0.01,  P<0.001.

Figure 15:
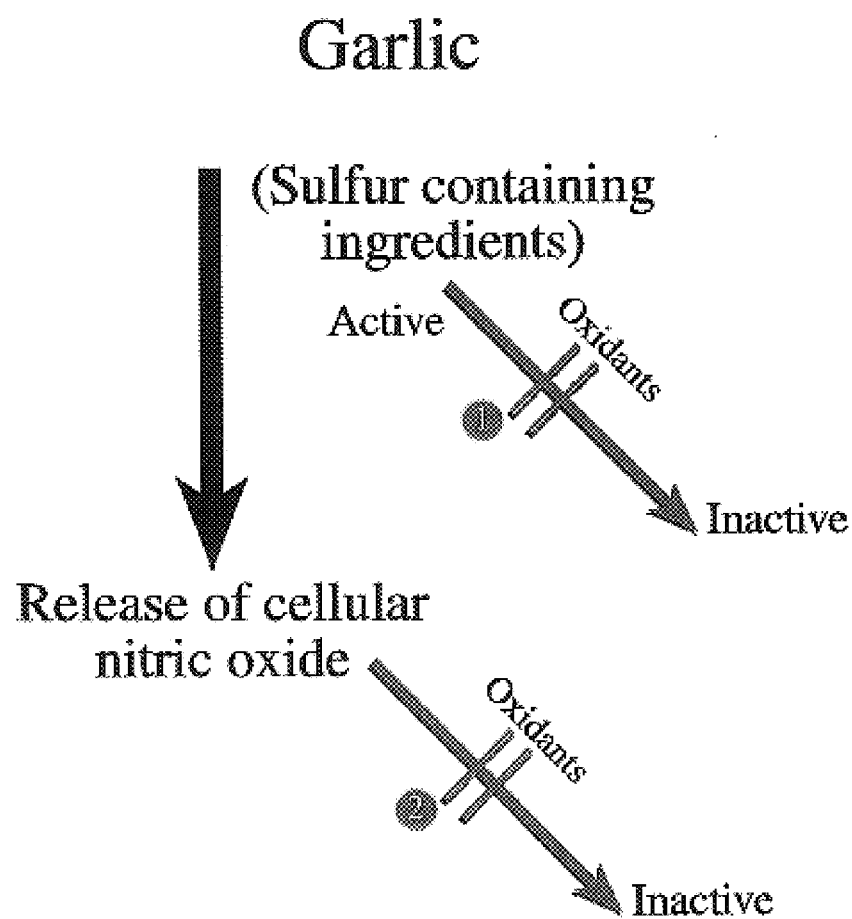

FIG. 15. Graph showing a working model for the potential mechanism of garlic related compounds and its potentiation by antioxidants on the inhibition of vascular and angiogenesis-mediated disorders.

SUMMARY OF THE INVENTION

An objective of the present invention is to provide a method for the prevention and treatment of vascular-related diseases such as vascular re-occlusion or restenosis pre- and post-arterial intervention procedures (balloon angioplasty or stent) and pathological angiogenesis-mediated disorders including cancer, ocular diseases (DR and AMD), and inflammatory diseases by the administration to a mammal a therapeutically effective amount of a combination of (i) garlic derived or related compounds or other natural/ synthetic sulfur (SH, Sulfate, Thioester, and other sulfur containing polyanionic) containing compounds and (ii) natural antioxidants. Preferred methods of the present invention involved the administration of garlic-related compounds (Alliin, allyl disulfide, diallyl trisulfide, S-allyl mercapto cysteine, and other thioallyl containing compounds) and antioxidants.

Another objective of the present invention is to provide a method of preventing and treating vascular-related diseases (vascular re-occlusion or restenosis) and pathological-mediated disorders such as cancer, ocular (DR and AMD), and inflammatory diseases in a mammal wherein the combination of (i) and (ii) above and optionally, (iii) minerals, are administered in amounts to provide a synergistic effect as a supplement for such patients. More specifically, such compositions can be used to treat patients with vascular disorders pre- and post-arterial intervention procedures and for cancer patients in conjunction with chemotherapeutics, radiotherapeutics, and other angiogenesis inhibitors such as integrin antagonists, endostatin, thalidomide, VEGF antagonists, and other mechanisms Also, the present invention compositions can be used as an adjunct to laser and other anti-angiogenesis (e.g., co-administration with angiostatic agents) for treating DR and AMD.

Combinations of (i), (ii), and optionally (iii) can be administered as pharmaceutical compositions for prevention or treatment of undesired angiogenesis, for instance for prevention of tumor metastasis or inhibition of primary tumor growth, for ocular disorders such as DR and AMD, and for inflammatory diseases such as rheumatoid arthritis (RA).

In another related embodiment, a tissue to be treated is retinal or macular tissue of a patient with diabetic retinopathy, macular degeneration or neovascular glaucoma. In an additional related embodiment, a tissue to be treated is a tumor tissue of a patient with a solid tumor, a metastasis, a skin cancer, a breast cancer, a hemangioma or angiofibroma and the like cancer for the inhibition of tumor-related angiogenesis. Typical solid tumor tissue treated by the present method includes lung, ovarian, pancreas, breast, colon, and the like tissues. In the absence of neovascularization, tumor tissue does not obtain the required nutrients, slow in growth, cease additional growth, regress, ultimately becomes necrotic, and no metastases because of the requirement of neovascularization for all of these processes.

In a related embodiment, the invention contemplates the practice of the method in conjunction with other therapies such as conventional chemotherapy directed against solid tumors and for the control of establishment of metastases. The administration of angiogenesis inhibitor is typically conducted during or after chemotherapy at a time where the tumor tissue will be responding to toxic assault by inducing angiogenesis to recover by the provision of a blood supply and nutrients to the tumor tissue. Additionally, it is preferred to administer this angiogenesis inhibition method after surgery where solid tumors have been removed as a prophylaxis against metastases.

Restenosis is a process of smooth muscle cell migration and proliferation at the site of percutaneous transluminal coronary angioplasty, which hinder the success of angioplasty. The migration of smooth muscle cells during restenosis can be considered a process of angiogenesis, which is inhibited by the present methods. Therefore, the invention also contemplates inhibition of restenosis by inhibiting smooth muscle migration and inhibiting angiogenesis in the atherosclerotic lesion that leads to plaque rupture. For inhibition of restenosis, the combination of the garlic containing sulfhydryl (Alliin and derivatives), antioxidants (vitamin C & E) and minerals (selenium) to be administered after angioplasty/stent procedures for up to 6 months or longer.

DETAILED DESCRIPTION OF THE INVENTION

The present invention is directed to compositions and methods of use in the prevention and treatment of vascular-related diseases and disorders and cancer. More specifically, the compositions comprise the administration of (i) one or more garlic-derived or related compounds and (ii) one or more antioxidants. Methods of use involve the administration to a mammal of one or compositions of the present invention.

The garlic-derived or related compounds of the present invention are those compounds extracted from garlic that contain SH moieties ("garlic containing sulfhydryl compounds"). Examples of such compounds include alliin, allicin, ajoene, and allyl disulfide, dialyl trisulfide, and other -SH containing compounds from either natural or synthetic sources. The garlic-derived or related compounds can also include synthetically modified garlic-sulfhydryl compounds, obtained by methods known in the art. For example, allicin may be modified by the addition of a carboxyl group containing acids to its SH group in order to yield a thioester. Such synthetically modified compounds may provide a "pro-drug" effect, wherein the compound is protected from oxidation or other degradation prior to being activated in vivo by release of the protecting group on its SH moiety.

The antioxjdants of the present invention are biologically compatible and, preferably, can be taken orally. Examples of antioxidants of the present invention include, but are not limited to, vitamins C, E, coenzymeQ10, grape seed extracts, flavanoids, GSH, EDU and other natural or synthetic antioxidants.

As stated above, preferred compositions and methods of the present invention involve the additional inclusion of minerals. Examples of minerals useful in the present invention include, but are not limited to, selenium and magnesium.

As used herein, "active agent" refers individually to, or the combination of, the garlic sulfhydryl compounds and antioxidants and, optionally in addition, the minerals, of the present invention.

The route of administration (e.g., topical, parenteral or oral) and the dosage regimen will be determined by skilled clinicians, based on factors such as the exact nature of the condition being treated, the severity of the condition, the age and general physical condition of the patient, and so on.

Dosage forms of compositions suitable for administration contain from about 1 mg to about 100 mg of active ingredient per unit dose. In these pharmaceutical compositions the active ingredient will ordinarily be present in an amount of about 0.595% by weight based on the total weight of the composition. The active ingredient can be administered orally in solid dosage forms, such as capsules, tablets and powders, or in liquid dosage forms, such as elixirs, syrups and suspensions. It can be administered parenterally, in sterile liquid dosage forms. Compositions of the present invention may also be administered topically, in the form of ointments and creams.

Gelatin capsules contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract. Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts, and sodium EDTA. In addition, parenteral solutions can contain preservatives, such as benzalkonium chloride, methyl- or propyl-paraben and chlorobutanol. Suitable pharmaceutical carriers are described in Remington's Pharmaceutical Sciences, 17th ed., Mack Publishing Company, Easton, Pa., 1985, a standard reference text in this field, the contents of which are incorporated herein by reference.

Examples of pharmaceutical dosage-forms for administration of the compounds of this invention can be illustrated as follows:

Capsules

A large number of unit capsules can be prepared by filling standard two-piece hard gelatin capsules each with 0.1 to 100 mg of powdered active ingredient, 150 mg of lactose, 50 mg of cellulose, and 6 mg magnesium stearate.

Soft Gelatin Capsules

A mixture of active ingredient in a digestible oil such as soybean oil, cottonseed oil or olive oil can be prepared and injected by means of a positive displacement pump into gelatin to form soft gelatin capsules containing 0.1 to 100 mg of the active ingredient. The capsules should then be washed and dried.

Tablets

A large number of tablets can be prepared by conventional procedures so that the dosage unit is 0.1 to 100 mg of active ingredient, 0.2 mg of colloidal silicon dioxide, 5 milligrams of magnesium stearate, 275 mg of microcrystalline cellulose, 11 mg of starch and 98.8 mg of lactose. Appropriate coatings may be applied to increase palatability or delay absorption.

Suspension

An aqueous suspension can be prepared for oral administration so that each 5 mL contain 0.1 to 100 mg of finely divided active ingredient, 200 mg of sodium carboxymethyl cellulose, 5 mg of sodium benzoate, 1.0 g of sorbitol solution, U.S.P., and 0.025 mg of vanillin.

Injectable

A parenteral composition suitable for administration by injection can be prepared by stirring 0.1 to 100 mg by weight of active ingredient in 10% by volume propylene glycol and water. The solution is sterilized by commonly used techniques.

The combined active ingredients of this invention may be formulated such that, although the active ingredients are combined in a single dosage unit, the physical contact between the active ingredients is minimized. In order to minimize contact, for example, where the product is orally administered, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. Another embodiment of this invention where oral administration is desired provides for combined compounds wherein one of the active ingredients is coated with a sustained-release material which effects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of combined compounds in which the one compound is coated with a sustained and/or enteric release polymer, and the other compound is also coated with a polymer such as a low viscosity grade of hydroxypropyl methylcellulose or other appropriate materials as known in the art, in order to further separate the active components. The polymer coating serves to form an additional barrier to interaction with the other component.

Dosage forms of the combination products of the present invention wherein one active ingredient is enteric coated can be in the form of tablets such that the enteric-coated compound and the other active ingredient are blended together and then compressed into a tablet or such that the enteric coated component is compressed into one tablet layer and the other active ingredient is compressed into an additional layer. In addition, dosage forms of the present invention can be in the form of capsules wherein one active ingredient is compressed into a tablet or in the form of a plurality of microtablets, particles, granules or non-perils, which are then enteric coated. These enteric coated microtablets, particles, granules or non-perils are then placed into a capsule or compressed into a capsule along with a granulation of the other active ingredient.

These as well as other ways of minimizing contact between the combined compounds, whether administered in a single dosage form or administered in separate forms but at the same time or concurrently by the same manner, will be readily apparent to those skilled in the art, based on the present disclosure.

Combination:

Each therapeutic compound of this invention can independently be in any dosage form, such as those described above, and can also be administered in various ways, as described above. For example, the compounds may be formulated together, in a single dosage unit (that is, combined together in one capsule, tablet, powder, or liquid, etc.) as a combination product As is appreciated by a medical practitioner skilled in the art, the dosage of the combination therapy of the invention may vary depending upon various factors such as the pharmacodynamic characteristics of the particular agent and its mode and route of administration, the age, health and weight of the recipient, the nature and extent of the symptoms, the kind of concurrent treatment, the frequency of treatment, and the effect desired, as described above. By way of general guidance, typically a daily dosage may be about 0.01 milligram to about 1 gram of each component.

In general, the doses utilized for the previously described purposes will vary, but will be in an effective amount to inhibit or reduce neovascularization. As used herein, the term "therapeutically effective amount" is that amount of an active agent, which inhibits formation of new blood vessels or reduces the number of blood vessels involved in the pathological condition. The active ingredients will normally be contained in these formulations in an amount from about 0.01 to about 10.0 weight/percent. Preferable concentrations range from about 0.1 to about 5.0 weight/percent. Thus, for topical administration, these formulations are delivered to the disease site one to six times a day, depending on the routine discretion of the skilled clinician. Systemic administration, for example, in the form of tablets or suppositories is useful for the treatment of polyp formation. Tablets containing 1 to about 1000 mg of a compound can be taken 1–6 times per day depending on the discretion of the skilled clinician.

The compositions may also be formulated such that the individual active agents act synergistically. For example, the compositions of the present invention may also be formulated such that the individual agents if dosed separately would comprise a sub-therapeutic dose. As used herein, "sub-therapeutic dose" refers to an amount of an active agent that would not provide treatment, prevention of amelioration of the condition to be treated or prevented if dosed alone, without other active agents.

The compositions of the present invention are useful in inhibiting pathological neovascularization in human patients. As used herein, the term "pathological neovascularization" refers to those conditions wherein the formation of blood vessels (neovascularization) is harmful to the patient. Examples of pathological neovascularization dependent diseases include: ocular disorders (DR, AMID), cancer, arthritis, arteriosclerosis, and other pathological angiogenesis-mediated disorders.

The compositions and methods of the present invention are also useful in preventing and treating any ocular neovascularization, including, but not limited to: retinal diseases (diabetic retinopathy, chronic glaucoma, retinal detachment, sickle cell retinopathy and subretinal neovascularization due to senile macular degeneration); rubeosis iritis; proliferative vitreo-retinopathy; inflammatory diseases, neoplasms (retinoblastoma, pseudoglioma and melanoma); Fuchs' heterochromic iridocyclitis; neovascular glaucoma; corneal neovascularization (inflammatory, transplantation and developmental hypoplasia of the iris); neovascularization following a combined vitrectomy and lensectomy; vascular diseases (retinal ischemia, choroidal vascular insufficiency, choroidal thrombosis and carotid artery ischemia); neovascularization of the optic nerve, and neovascularization due to penetration of the eye or contusive ocular injury.

Preferred methods of the present invention involve the administration of compositions of the present invention for the treatment, prevention or amelioration of DR, AMD, and rheumatoid arthritis (RA).

EXAMPLES

The purpose of this study was to determine whether SH-containing by garlic might abrogate pro-angiogenic factors induced angiogenic responses in vitro and in vivo. Also, the purpose of this study was to determine if the combination of garlic and antioxidants may play an important role in the inhibition of vascular-related effects and angiogenesis.

For the different in vitro assays human smooth muscle cells and human umbilical vein endothelial (HUVEC) cells were obtained from (Clonetics, Walkersville, Md.). Endothelial cells (EC) were grown to 80–90% confluence in Endothelial Growth Medium (EGM) containing hEGF 10 ng/ml, hydrocortisone 1 mg/ml, gentamicin 50 mg/ml, amphotercin-B 50 ug/ml, Blood Brain Extract 0.012 mg/ml and 2% Fetal Bovine Serum equilibrated with 95% air/5% $CO_2$ at 37° C. HUVEC cells will be serially passed in Endothelial Growth in cell culture flasks coated with gelatin 0.2%, (Sigma, St. Louis, Mo.). Confluent cultures of endothelial cells between the $3^{rd}$ and $6^{th}$ passages were washes with HBSS and harvested using 0.025% trypsin/0.01% EDTA and counted by hemacytometer. EC were re-suspended in 24 well plates coated with Matrigel matrices or directly on 96-well cell culture plates. EC were incubated 72 hours in basal media or growth media.

Endothelial Cell Tube Formation: Matrigel Growth Factor Reduced (GFR), (Becton Dickinson, Bedford, Mass.) was thawed overnight at 4° C. Using cold pipette tips, 250 $\mu$l of Mitragel GFR was placed in a cold 24-well multi-well plate, (Falcon or Nunc). Matrigel GFR was allowed to polymerize during incubation at 37° C. for 30 minutes. Cells were trypsinized, centrifuged and subsequently washed twice in PBS. After counting, HUVE cells were plated at 40,000 cells/well in EBM containing FGF2 50 ng/ml at an initial volume of 125 ul in a 24-well plate (Corning). Following 1–2 hrs of incubation at 37° C. 5% $CO_2$ and 95% humidity to allow cell attachment, 125 ul samples containing varied concentrations of alliin, allyl disulfide or diallyl trisulfide dissolved in EBM media were added. Plates were incubated overnight at 37° C. 5% $CO_2$ and 95% humidity. Subsequently, the media was removed and cells were fixed and stained using a modified Hema 3 Stain kit (Fisher, Swedesboro, N.J.)

Microscopic Analysis of Endothetial Cell Tube Formation: Chorioallantoic membrane (CAM) tissue directly beneath FGF2-saturated filter disk was resected. Tissues were washed three times with PBS. Sections were placed in a 35-mm petri dish (Nalge Nunc, Rochester, N.Y.) and examined under a SV6 stereomicroscope (Karl Zeiss, Thornwood, N.Y.) at 50x magnification. Digital images of microtiter well sections were collected using a 3-CCD color video camera system (Sony, America, New York, N.Y.) and analyzed with the Image-Pro Plus software (Media Cybernetics, Silver Spring, Md.). The area and major axis length of stained cells having a tubular morphology on the Matrigel surface counted from 5 images/well. Area data is expressed in units of $10^4$ square microns and length data is expressed as length/area in units of $mm/mm^2$. Percent inhibition data is expressed as the quotient of the experimental value minus the negative control value (EBM media) divided by the difference between the positive control and the negative control values.

In Vivo Angiogenesis: Ten-day old chick embryos were purchased from Spafas, Inc. (Preston, Conn.) and were incubated at 37° with 55% humidity generally referred to as chick chorioallantoic membrane (CAM) model. A small hole was punctured in the shell concealing the air sac with a hypodermic needle. A second hole was punctured in the shell on the broadside of the egg directly over an avascular portion of the embryonic membrane, as observed during candling. A false air sac was created beneath the second hole by the application of negative pressure to the first hole, which caused the CAM to separate form the shell. A window, approximately 1.0 cm2, was cut the in the shell over the dropped CAM with the use of a small crafts grinding wheel (Dermal, Division of Emerson Electric Company (Racine, Wis.) which allowed direct access to the underlying CAM.

Angiogenesis can be induced on the CAM after normal embryonic angiogenesis has resulted in the formation of mature blood vessels. Angiogenesis has been shown to be induced in response to specific cytokines or tumor fragments as described by Leibovich et al., Nature, 329: 630 (1987) and Ausprunk et al., Am. J. Pathol., 79: 597 (1975).

Filter disks of #1 filter paper (Whatman International, United Kingdom) were soaked in 3 mg/ml cortisone acetate (Sigma, St. Louis, Mo.) in a solution of 95% ethanol and water and subsequently air dried under sterile conditions. FGF2 (Life Technologies, Gaithersburg, Md.) was used to grow vessels on the CAMs of 10-day old chick embryos. Sterile filter disks adsorbed with FGF2 dissolved in PBS at 1 ug/ml were placed on growing CAMs. At 24 hrs, test compounds or control vehicle was added to CAMs topically or by intravenous injection. A range of 0.01–0.11 mg in 25 $\mu$l of the garlic sulfhydryl compound, alliin, or 25 $\mu$l of buffered saline were applied to the growth factor saturated filter 24 hours later. Additionally, alliin (at a final serum concentration of 0.01–0.11 mg) was also injected intravenously into the chick circulation 24 hours later. CAMs were harvested on the fourth day of stimulation. Blood vessel branch points in the 5 mm filter disk area were counted at 30× magnification in a blinded fashion as a size-independent quantitative indicator of vascular sprouting in response to growth factors. As angiogenesis is characterized by the sprouting of new vessels in response to growth factors, counting blood vessel branch points is a useful quantitative means of obtaining an angiogenic index. See Auspruck et al., Am. J. Pathol., 79: 597–618 (1975) and Ossonski et al., Cancer Res., 40: 2300–2309 (1980). At least ten embryos were used per treatment group. Data was evaluated in terms of average number of blood vessel branch points per treatment group±standard deviation of measurement. Statistical analyses were performed using Student's t-test. Representative CAMS from each treatment group was photographed at 10× magnification.

As demonstrated herein, the CAM assay illustrates inhibition of neovascularization based on both the amount and extent of new vessel growth. Furthermore, it is easy to monitor the growth of any tissue transplanted on the CAM, such as tumor tissues. Finally, the assay is particularly useful because there is an internal control for toxicity in this assay system. The chick embryo is exposed to any test agents, and therefore the health of the embryo is an indication of toxicity. Other assays that measure the presence of angiogenesis include, rabbit eye assay. See D'Amato, et al., Proc. Natl. Acad. Sci., 91: 4082–4085 (1994). Additionally, other assays that measure tumor angiogenesis include the chimeric mouse assay. Others have described this assay in detail. See Yan, et al., J. Clin. Invest., 91: 986–996 (1993).

Microscopic Analysis of CAM Sections: CAM tissue directly beneath FGF2-saturated filter disk was resected from embryos treated 48 hours prior with compounds or controls. Tissues were washed three times with PBS. Sections were placed in a 35-mm petri dish (Nalge Nunc, Rochester, N.Y.) and examined under a SV6 stereomicroscope (Karl Zeiss, Thornwood, N.Y.) at 50× magnification. Digital images of CAM sections adjacent to filters were collected using a 3-CCD color video camera system (Toshiba America, New York, N.Y.) and analyzed with the Image-Pro Plus software (Media Cybernetics, Silver Spring, Md.). The number of vessel branch points contained in a circular region equal to the area of a filter disk was counted for each section. Percent inhibition data is expressed as the quotient of the experimental value minus the negative control value divided by the difference between the positive control value and the negative control value.

Chick Chorioallantoic Membrane Tumor Assay Model:

In addition to the angiogenesis assays described above where the effect of the garlic sulfur containing ingredient Alliin±antioxidants were evaluated, the anti-tumor efficacy for Alliin+antioxidants were evaluated as well. Ten million tumor cells were placed on the surface of each CAM and were cultured for one week. The resulting tumors were excised and cut into 50 mg fragments. Cheresh et al., Cell 58: 945–953 (1989), Brooks et al., J. Cell Biol., 122:1351 (1993) and as described herein. These fragments were placed on additional CAMs and treated topically the following day with 0.11 mg in 25 $\mu$l of Alliin with and without anti-oxidant or saline. Forty eight hours later, CAMs were excised from the egg and the number of blood vessels entering the tumors were counted (as vessel branch points).

Data presented as mean blood vessel number per treatment group (+/− standard error of measurement). Each treatment group incorporated at least ten tumors per experiment. Representative tumors were photographed at 10× magnification. Tumors were then excised from the egg and tumor weights were determined for each tumor. Data presented as mean tumor weight per treatment group (+/− standard error of measurement). Statistical analyses were performed using Student's t-test.

Effect on Apoptosis:

Apoptosis can be detected by a variety of methods, which include direct examination of DNA isolated from tissue to detect fragmentation of the DNA. Analysis of DNA Fragmentation: Angiogenesis was induced by placing filter disk saturated with FGF2 on the CAMs of 10-days old embryos as described previously. DNA fragmentation was detected by resecting the CAM tissue directly below FGF2 saturated filter disk 48 hours after the administration of the garlic containing sulfhydryl ingredients. Resected CAM tissues were washed three times with sterile PBS and finally minced, resuspended in 0.25% bacterial collagenase (Worthington Biochemical, Freehold, N.J.) and incubated for 90 minutes at 37° C. with occasional vortexing. DNA was extracted from single cell suspension as previously described. Bissonette et al., Nature, 359:552 (1992). Briefly, equal numbers of CAM cells were lysed in 10 mM tris-HCL, pH 8.0, 10 mM EDTA in 0.5% (v/v) Triton X-100 (sigma, St. Louis, Mo.). Cell lysates were centrifuged at 16,000× g for 15 minutes at 4° C. to separate soluble fragmented DNA from the intact chromatin pellet. Fragmented DNA was washed, precipitated, and measured.

The foregoing written specification is considered to be sufficient to enable one skilled in the art to practice the invention. The present invention is not to be limited in scope by the cell used, since the deposited embodiment is intended as a single illustration of one of the aspect of the cell invention and any cell line that is functionally equivalent is within the scope of this invention From this investigation, evidences are provided that garlic sulfhydryl compounds modulate vascular-related effects (effects on smooth muscle cell migration as shown in FIGS. 4–6) and angiogenesis-related processes and mechanisms (FIGS. 7–15). Finally, these studies revealed for the first time that garlic sulfhydryl compounds in combination with antioxidants may be useful for the treatment and prevention of vascular-related diseases and disorders and solid tumors in cancer patients, in addition to other angiogenesis-mediated disorders.

Inhibition of in vitro Endothelial Tube formation by Garlic Sulfhydryl Compound: The later phases of neovascularization require EC to undergo morphological changes that give rise to tubular structures possessing lumens. Cultures of HUVEC were plated at a sub-confluent level on solidified Mitragil in 24-well plates and incubated in the presence of FGF2 (50 ng/ml) and alliin (0–0.011 mg). HUVEC cultured in this assay form tube-like structure on the surface of the matrix. By contrast HUVEC treated with alliin failed to develop the level of tubes associated with control cultures. Quantitative measurements of tube formation revealed that the garlic sulfhydryl compound, alliin inhibited the cytokine stimulated tube formation by 90–100%. The results demonstrate that the inhibitory effects of Garlic ingredient may lie in their ability to prevent this critical step in the angiogenic process, In the presence of FGF2 alone, adjacent CAM membranes undergo morphological changes and become vascularized. The extent of neovascularization in FGF2 treated is approximately 2–3 fold greater than control CAMs. Angiogenesis was stimulated on the CAM with filter paper disks saturated in bFGF. Twenty-four hours later alliin with and without anti-oxidant were directly applied to the growth factor saturated filter. After three days, CAMs were excised and blood vessels were quantified by counting vessel branch points, as described (Brooks, et. al., 1999). The counting of blood vessel branch points provides a size-independent measure of the sprouting of new vessels that occurs during angiogenesis. The garlic sulfhydryl compound, alliin was able to inhibit the growth of new blood vessels induced by bFGF by 92 +/−10% (p<0.001), whereas the antioxidant alone did not have any effect on angiogenesis (8+/−5% inhibition).

Figure 1:
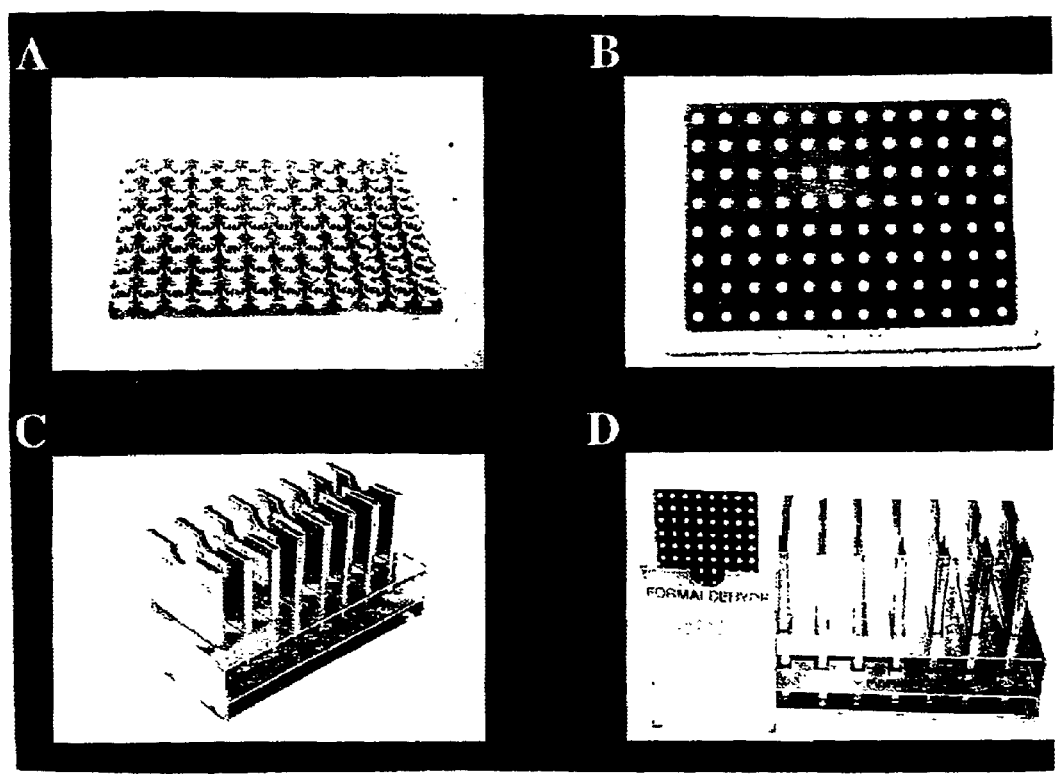
FIG. 1. Graph showing the modified Boyden chamber used to examine the effect of garlic ingredients, antioxidants, and combinations on human smooth muscle cell migration toward plasma obtained from acute myocardial infarction patients (MI) during balloon angioplasty and stent coronary intervention.

Garlic Ingredient Alliin block angiogenesis in vivo:

To establish whether alliin might modulate angiogenesis, the abilities of alliin with and without anti-oxidant on growth factor-induced angiogenesis in the chick CAM model was investigated. Twenty-four hours after stimulating angiogenesis on the CAM with bFGF, alliin with and without anti-oxidant were directly applied to the growth factor saturated filter disk or were injected intravenously into the embryonic circulation. As shown in FIG. 1, alliin blocked bFGF-induced angiogenesis on the CAM by at least 92+/−10% (p<0.001) whereas anti-oxidant alone had no significant effect.

Garlic Sulfhydryl Compound, Alliin Blocks Tumor-induced angiogenesis and inhibit tumor growth: Angiogenesis is a highly regulated process that is critical for development and wound healing-in the adult organism, angiogenesis remains placid for the most part with a few exceptions, some physiological and some pathophysiological. This study identifies garlic ingredient as a potent inhibitor of the angiogenic process in vitro and in vivo. Thus, the notion that garlic may have a place in the therapeutic inhibition of angiogenesis associated with metastatic diseases, neovascular ocular and inflammatory diseases is supported by these findings.

Cancer and cardiovascular diseases are two pathological states involving uncontrolled proliferation of either tumor or vascular smooth muscle cells. Interestingly, both types of disease can be prevented by the same type of natural chemicals, such as sulfhydryl-containing compounds present in garlic. Alliin inhibited different types of tumor growth in the CAM model by inhibiting tumor-induced angiogenesis. Thus, Garlic might be a useful target for the inhibition of angiogenesis associated with human tumor growth, ocular, and inflammatory diseases Obviously, numerous modifications and variations of the present invention are possible in light of the above teachings. It is therefore to be understood that within the scope of the appended claims, the invention may be practiced otherwise than as specifically described herein.

What is claimed:

1. A method of treating pathological neovascularization is in a mammal comprising administering to a mammal a therapeutically effective amount of a composition consisting essentially of a one or more gralic-sulfhydryl compounds and one or more antioxidants as active agents.

2. A method of claim 1 wherein the garlic-sulfhydryl compound(s) and the antioxidant(s) are contained in the composition in amounts that provide a synergistic effect to the treatment of the mammal.

3. The method of claim 1, wherein the garlic sulfhydryl compound is selected from the group consisting of alliin, allyl disulfide, allicin, ajoene diallyl trisulfide, S-allyl mercapto cysteine, and other thioallyl containing compounds and combinations thereof.

4. The method of claim 1, wherein the antioxidant is selected from the group consisting of Vitamin E, Vitamin C, coenzymeQ10, grape seed extract, flavanoids, GSH, EDU or combinations thereof.

5. A method for inhibiting angiogenesis in a tissue comprising administering to said tissue a composition comprising a therapeutically effective amount of a composition consisting essentially of a one or more garlic-sulfhydryl compounds and one or more antioxidants as active agents.

6. The method of claim 1 wherein the pathological neovascularization is arthritis.

7. The method of claim 5 wherein said tissue is a solid tumor or a solid tumor metastases and said angiogenesis is tumor angiogenesis.

8. The method of claim 5 wherein said tissue is retinal tissue or choridal tissue of a patient with diabetic retinopathy or macular degeneration.

9. The method of claim 5 wherein the garlic-sulfhydryl compound is in an amount from about 0.1 to 10 mg.

10. The method of clam 5 wherein said tissue is coronary, carotid or peripheral arteries at risk of restenosis.

11. The method of claim I wherein said administering comprises oral, transdermal, intranasal, intravenous, subcutaneous, or intramuscular routes.

\* \* \* \* \*